United States Patent [19]

Koert et al.

[11] 4,089,872
[45] May 16, 1978

[54] ANTIBIOTICS STEFFIMYCINOL AND 7-DEOXYSTEFFIMYCINOL AND PROCESS FOR PREPARING THE SAME

[75] Inventors: James M. Koert; Paul F. Wiley, both of Kalamazoo, Mich.

[73] Assignee: The Upjohn Company, Kalamazoo, Mich.

[21] Appl. No.: 775,856

[22] Filed: Mar. 9, 1977

[51] Int. Cl.² .............................................. C07C 49/72
[52] U.S. Cl. ................................................... 260/365
[58] Field of Search ................................. 260/365, 383

[56] References Cited

U.S. PATENT DOCUMENTS

| | | | |
|---|---|---|---|
| 3,590,028 | 6/1971 | Arcomone et al. | 260/365 X |
| 3,665,018 | 5/1972 | Jolles | 260/365 |
| 3,721,684 | 3/1973 | Meyers et al. | 260/365 |
| 3,803,124 | 4/1974 | Arcomone et al. | 260/365 X |
| 3,976,667 | 8/1976 | Kelly | 260/365 |
| 4,012,448 | 3/1977 | Smith et al. | 260/365 X |
| 4,021,457 | 5/1977 | Kende et al. | 260/383 |

OTHER PUBLICATIONS

Arcomone et al., CA 74:142288b (1971).
Wong et al., *Can. J. Chem.*, vol. 49, No. 16, pp. 2712–2718 (Sep., 1971).

*Primary Examiner*—Daniel E. Wyman
*Assistant Examiner*—Thomas G. Waltz
*Attorney, Agent, or Firm*—Roman Saliwanchik

[57] ABSTRACT

Antibiotics steffimycinol and 7-deoxysteffimycinol produced by reduction of the antibiotic steffimycinone. Steffimycinol is active against various microorganisms, for example, *Bacillus subtilis, Mycobacterium avium* and *Streptococcus pyogenes*; 7-deoxysteffimycinol is active against *Sarcina lutea, Bacillus cereus,* and *B. subtilis.* Thus, these antibiotics can be used to inhibit the growth of the above microorganisms in various environments.

10 Claims, No Drawings

ANTIBIOTICS STEFFIMYCINOL AND 7-DEOXYSTEFFIMYCINOL AND PROCESS FOR PREPARING THE SAME

The invention described herein was made in the course of, or under Contract NO1-CM-43753 with the National Cancer Institute, National Institutes of Health, Bethesda, Md. 20014.

BACKGROUND OF THE INVENTION

The process for preparing the antibiotic steffimycinone and the description of its various biological properties are disclosed in U.S. Pat. No. 3,976,667.

The structure of steffimycinone can be shown as follows:

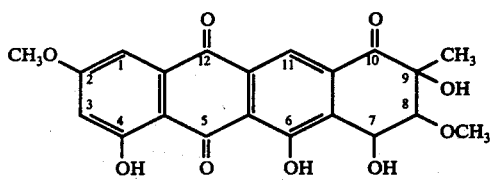

BRIEF SUMMARY OF THE INVENTION

Steffimycinol and 7-deoxysteffimycinol can be prepared by reduction of steffimycinone. Both antibiotics are biologically active, as disclosed above, and can be used in various environments to inhibit the growth of susceptible microorganisms. For example, steffimycinol and 7-deoxysteffimycinol can be used for treating breeding places of silkworms, to prevent or minimize infections which are well known to be caused by *Bacillus subtilis*. 7-Deoxysteffimycinol can be used in paper-mill operations to control the contamination of wool by the microorganism *Bacillus cereus*. Steffimycinol can be used to control *Mycobacterium avium* which is a known producer of generalized tuberculosis in birds and rabbits.

DETAILED DESCRIPTION

Steffimycinol and 7-deoxysteffimycinol have the following structures:

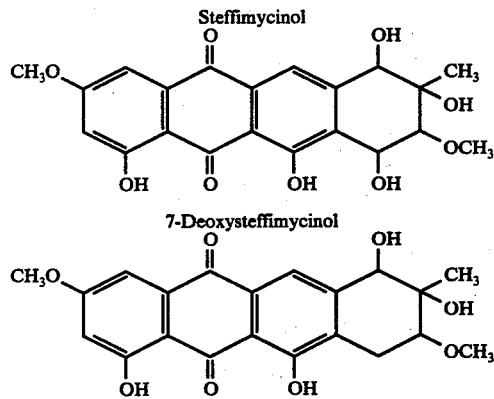

Steffimycinol can be prepared by reacting steffimycinone with a metal hydride, for example, $NaBH_4$ in an alkaline solution. The reduction process also can be conducted with aluminum isopropoxide in place of the metal hydride. The reduction is carried out by using one mole or less of the metal hydride per mole of steffimycinone. Steffimycinol is isolated from the reaction mixture by extraction with a suitable solvent for steffimycinol, for example, a lower alkyl acetate, wherein the lower alkyl is from 1–5 carbon atoms, inclusive. The preferred solvent is ethyl acetate. The extracts containing steffimycinol are dried, filtered, and evaporated under reduced pressure to a residue. This material can be purified by use of silica gel chromatography with elution by the solvent system $CHCl_3$—MeOH (97:3 v/v). Active fractions are determined by thin-layer chromatography (tlc) on silica gel with $CHCl_3$—MeOH (95:5 v/v); $R_f$ is 0.19. Active fractions so determined are combined and evaporated under pressure to give a pure preparation of steffimycinol.

7-Deoxysteffimycinol can be prepared from steffimycinone by use of the same procedure, described above, with the exception that a large excess of metal hydride is used in the reduction. For example, a ratio of 5 moles of metal hydride per mole of steffimycinone can be used to prepare 7-deoxysteffimycinol. 7-Deoxysteffimycinol is recovered from the reaction mixture by solvent extraction, as described above for the recovery of steffimycinol. The material isolated by extraction is relatively pure but can be recrystallized from $CHCl_3$—MeOH (97:3 v/v) to give a purer preparation of 7-deoxysteffimycinol.

Steffimycinol and 7-deoxysteffimycinol can be acylated under standard acylating conditions with an appropriate acid halide or anhydride to give the acylated compounds. Under these standard conditions, steffimycinol is acylated at the 4, 6, 7, 9 and 10 hydroxyls and 7-deoxysteffimycinol is acylated at the 4, 6, 9 and 10 hydroxyls. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, terbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like: (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxy- hydrocarbon carboxylic acids include hydrocarboncarboxylic acids as given above which are substituted by one or more of halogen, nitro, hydroxy, amino, cyano, or thiocyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);

and the like.

The acylated compounds, as described above, can be used in animals for the same biological purposes as disclosed above for steffimycinol and 7-deoxysteffimycinol. For example, the acylated compounds can be given in oral form to an animal possessing the necessary enzyme to remove the acyl group, thus freeing the parent antibiotic compound which then inhibits susceptible bacteria.

Steffimycinol and 7-deoxysteffimycinol form salts with alkali metals and alkaline earth metals. Metal salts can be prepared by dissolving steffimycinol or 7-deoxysteffimycinol in methanol, adding a dilute metal base until the pH of the solution is about 9 to 11, and freeze drying the solution to provide a dried residue consisting of the metal salt. Metal salts can be, for example, the sodium, potassium, and calcium salts.

Steffimycinol and 7-deoxysteffimycinol salts, as described above, can be used for the same antibacterial purposes as steffimycinol and 7-deoxysteffimycinol.

The methyl ether of the phenolic hydroxyl groups on both steffimycinol and 7-deoxysteffimycinol can be prepared by methods well-known in the art. For example, the antibiotics can be reacted with dimethylsulfate and potassium carbonate in an acetone solution at room temperature for about 24 hours. The desired product can be recovered from the reaction mixture by evaporation of the acetone and partitioning of the residue between dilute base and chloroform or ethyl acetate. Evaporation of the organic phase followed by chromatography on silica gel using $CHCl_3$—MeOH (97:3 v/v) as the solvent system, gives the pure ether.

The above ethers can be used for the same antibacterial purposes as the parent compounds.

The following examples are illustrative of the process and products of the invention, but are not to be construed as limiting. All percentages are by weight and all solvent mixture proportions are by volume unless otherwise noted.

EXAMPLE 1 — STEFFIMYCINOL

Sixteen grams of steffimycinone is reduced in four equal batches by dissolving each batch in 200 ml of 0.2 N NaOH and adding to the solution dropwise with stirring over a period of 0.5 hr. a solution of 280 mg of $NaBH_4$ in 40 ml of 0.2 N NaOH. The reaction is stirred for another 0.5 hr. and 50 ml of 2.0 N HCl is added. The reaction mixture is extracted once with 200 ml of ethyl acetate and twice with 100 ml portions. The combined extracts are dried ($MgSO_4$), filtered, and evaporated under reduced pressure. A total of 13.2 g of residue is obtained. The residue is deposited on 37.1 g of silica gel from a $CHCl_3$—MeOH (9:1) solution. The silica gel is then added to a column of 1100 g of silica gel packed in $CHCl_3$—MeOH (97:3) and eluted with the same solvent system while collecting 20-ml fractions. Those fractions containing pure steffimycinol as judged by tlc on silica with $CHCl_3$—MeOH (95:5) are combined and evaporated under reduced pressure; yield 3.7 g of essentially pure steffimycinol; mp 230° dec.; $R_f$(tlc, above system) 0.19; uv EtOH λmax 227 nm ($\epsilon$ 35,400), 255 $_{sh}$ nm ($\epsilon$ 18,500), 269.5 nm ($\epsilon$ 21,220), 285 $_{sh}$ nm ($\epsilon$ 17,100), 435 nm ($\epsilon$ 13,100), 447 $_{sh}$ nm ($\epsilon$ 12,520); ir (Nujol) 3600, 3560, 3300, 1675, 1605, 1570, 1565, 1395, 1300, 1275, 1255, 1215, 1160 and 1100 $cm^{-1}$; mass spectrum (m/e) 416; $^1$H NMR ($CD_3SOCD_3$—$D_2O$) δ 1.38 (s, 3H, $CH_3C$), δ 3.33 (d, 1H, CHO, J=6.5 Hz), δ 3.64 (s, 3H, $CH_3O$), δ 3.83 (s, 3H, $CH_3O$), δ 4.45 (s, 1H, CHO), δ 4.96 (d, 1H, CHO, J=6.5 Hz), δ 6.62 (d, 1H, aromatic, J=2.5 Hz), δ 6.97 (d, 1H, aromatic, J=2.5 Hz), δ 7.77 (s, 1H, aromatic); $^{13}$C NMR ($CD_3SOCD_3$) δ 23.2 ($CH_3C$), δ 57.8, 61.9 (2$CH_3O$), δ 70.6, 74.3, 76.7, 89.0 (CHO), δ 107.8, 109.1, 111.2, 114.9, 119.5, 132.6, 134.7, 136.2, 150.4, 161.3, 165.8, 167.6 (aromatic, δ 182.2, 191.5 (carbonyl).

Anal. Calcd. for $C_{21}H_{20}O_9$: C, 60.60; H, 4.85. Found: C, 59.00; H, 4.77.

EXAMPLE 2 - 7—DEOXYSTEFFIMYCINOL

A solution of 920 mg (24.2 mmoles) of $NaBH_4$ in 46 ml of 0.2 N NaOH is added dropwise with stirring at room temperature to a solution of 2.0 g (4.83 mmoles) of steffimycinone in 100 ml of 0.2 N NaOH. The stirring is continued for 1 hour after addition is complete. The reaction mixture is mixed with 150 ml of ethyl acetate and acidified with 35 ml of 2 N HCl. The organic layer is drawn off, and the aqueous layer is extracted with two 100-ml portions of ethyl acetate. The combined ethyl acetate extracts are dried ($MgSO_4$), filtered, and evaporated under reduced pressure; yield 1.53 g of 7-deoxysteffimycinol. Material (2.2 g) prepared in this way is recrystallized twice from CHCl₃—MeOH (97:3); yield 1.12 g of 7-deoxysteffimycinol; mp 274°-276°; $R_f$ (tlc, CHCl₃—MeOH; 95:5) 0.45; uv EtOH λmax 226 nm (ε 34,000), 249 $_{sh}$ nm (ε 17,550), 273 nm (ε 24,500), 435 nm (ε 13,500), 449 $_{sh}$ nm (ε 12,800); ir (Nujol) 3490, 1660, 1625, 1610, 1560, 1390, 1315, 1300, 1275, 1240, 1210, 1190, 1095, 970, 805, 785, and 760 cm⁻¹; mass spectrum (m/e) 400.1172 (calcd. for C₂₁H₂₀O₈ 400.1158); ¹H NMR (CD₃SOCD₃) δ 1.35 (s, 3H, CH₃C), δ 3.43 (s, 3H, CH₃O), δ 3.2–3.5 (m, 3H, CHO, and CH₂), δ 3.87 (s, 3H, CH₃O), δ 4.27 (s, 1H, CHO), δ 6.73 (d, 1H, aromatic, J=2.5 Hz), δ 7.0 (d, 1H, aromatic, J=2.5 Hz), δ 7.7 (s, 1H, aromatic).

Anal. Calcd. for C₂₁H₂₀O₈: C, 63.00; H, 5.04. Found: C, 62.51; H, 4.99.

Steffimycinol and 7-deoxysteffimycinol have the antibacterial activities, hereinafter shown, as determined on a standard disc (7.0 mm) plate assay. All organisms were incubated at 32° C. except for *M. avium* which was 37° C. They were incubated for 16–18 hours.

| *S. lutea* and *B. cereus* medium | |
|---|---|
| Gelysate Peptone | 0.6 % |
| Trypticase Peptone®[1] | 0.4 % |
| Yeast Extract | 0.3 % |
| Beef Extractives | 0.15 % |
| Dextrose | 0.1 % |
| Agar | 1.5 % |

[1]Obtained from BBL Division of Becton, Dickinson & Co., Cockeysville, Maryland 21030 U.S.A.

| *M. avium* medium Brain and Heart Infusion Agar (All wts./liter) | |
|---|---|
| Calf Brains, infusion from | 200 g |
| Beef Hearts, infusion from | 250 g |
| Proteose Peptone, Difco | 10 g |
| Bacto-Dextrose | 2 g |
| NaCl | 5 g |
| Na₂HPO₄ | 2.5 g |
| Agar | 15 g |

| *B. subtilis* synthetic medium | |
|---|---|
| Na₂HPO₄ . 7H₂O | 1.5 g/liter |
| KH₂PO₄ | 4.3 g/liter |
| (NH₄)₂SO₄ | 1.0 g/liter |
| MgSO₄ | 0.1 g/liter |
| Glucose | 2.0 g/liter |
| Agar | 15.0 g/liter |
| Distilled Water | 1 liter |
| Metallic ion stock solution[1] | 1 ml/liter |
| Final pH | 6.2 |

[1]Metallic ion stock solution

| Compound | Concentration |
|---|---|
| NaMoO₄ . 2H₂O | 200 mcg/ml |
| CoCl₂ | 100 mcg/ml |
| CuSO₄ | 100 mcg/ml |
| MnSO₄ | 2 mg/ml |
| CaCl₂ | 25 mg/ml |
| FeCl₂ . 4H₂O | 5 mg/ml |
| ZnCl₂* | 5 mg/ml |

*ZnCl₂ has to be dissolved separately using a drop of 0.1 N HCl for 10 ml of water.

| Antibacterial Activity of Steffimycinol and 7-Deoxysteffimycinol Tested In Vitro Using 7mm Antibiotic-Impregnated Discs (Antibiotics Applied to Discs at 100 μg per ml) | | |
|---|---|---|
| | Inhibitory Zone Size (mm)* | |
| Organism | Steffimycinol | 7-Deoxysteffimycinol |
| *Bacillus subtilis* (synthetic medium) | 15 | 0 |
| *B. subtilis*, 209 (synthetic medium) | 21 | 3 |
| *Bacillus cereus* | 0 | 6 |
| *Sarcina lutea* | 0 | 5 |
| *Streptococcus faecalis* | 2 | 0 |
| *Streptococcus pyogenes* | 9 | 1 |
| *Mycobacterium avium* | 5 | 0 |
| *Proteus vulgaris* | 5 | 0 |
| *Escherichia coli* | 0 | 0 |

*Zone size minus 7mm.

We claim:

1. Steffimycinol, a compound having the following structure:

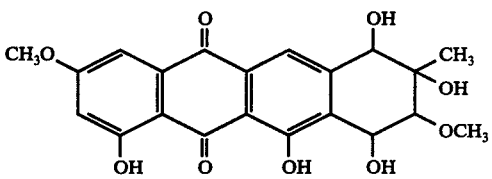

and alkali and alkaline earth metal salts thereof.

2. 7-Deoxysteffimycinol, a compound having the following structure:

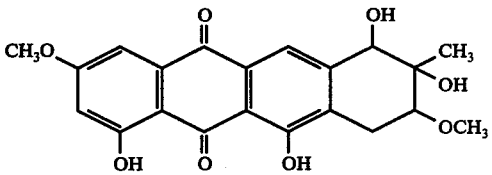

and alkali and alkaline earth metal salts thereof.

3. Tetra-O-acylates of the compound defined in claim 1 wherein said acyl group consists of a hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

4. Tri-O-acylates of the compound defined in claim 2 wherein said acyl group consists of a hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

5. A process for preparing the compound of claim 1 which comprises reduction of steffimycinone with one mole or less of a metal hydride or aluminum isopropoxide.

6. A process, according to claim 5, wherein NaBH₄ is the metal hydride.

7. A process, according to claim 5, wherein one mole or less of the metal hydride is used per mole of steffimycinone.

8. A process for preparing the compound of claim 2 which comprises reduction of steffimycinone with a large excess of a metal hydride or aluminum isopropoxide.

9. A process, according to claim 8, wherein NaBH₄ is the metal hydride.

10. A process, according to claim 8, wherein about 5 moles of the metal hydride is used per mole of steffimycinone.

* * * * *